(12) United States Patent
Jonczyk et al.

(10) Patent No.: US 9,382,244 B2
(45) Date of Patent: Jul. 5, 2016

(54) 7-AZAINDOLE-2,7-NAPHTHYRIDINE DERIVATIVE FOR THE TREATMENT OF TUMOURS

(71) Applicant: Merck Patent GmbH, Darmstadt (DE)

(72) Inventors: Alfred Jonczyk, Darmstadt (DE); Frank T. Zenke, Darmstadt (DE); Christiane Amendt, Muehltal/Trautheim (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 14/432,767

(22) PCT Filed: Sep. 9, 2013

(86) PCT No.: PCT/EP2013/002696
§ 371 (c)(1),
(2) Date: Apr. 1, 2015

(87) PCT Pub. No.: WO2014/053208
PCT Pub. Date: Apr. 10, 2014

(65) Prior Publication Data
US 2015/0252041 A1  Sep. 10, 2015

(30) Foreign Application Priority Data

Oct. 2, 2012 (DE) .......................... 10 2012 019 369

(51) Int. Cl.
| | |
|---|---|
| *C07D 471/04* | (2006.01) |
| *A61K 31/4375* | (2006.01) |
| *C07D 519/00* | (2006.01) |
| *A61K 45/06* | (2006.01) |

(52) U.S. Cl.
CPC .......... *C07D 471/04* (2013.01); *A61K 31/4375* (2013.01); *A61K 45/06* (2013.01); *C07D 519/00* (2013.01)

(58) Field of Classification Search
CPC ......................... C07D 471/04; A61K 31/4375
USPC .......................................... 546/122; 514/300
See application file for complete search history.

(56) References Cited

U.S. PATENT DOCUMENTS 8,981,101 B2 * 3/2015 Dorsch ................ C07D 471/04
546/113
2013/0310391 A1   11/2013 Dorsch et al.

FOREIGN PATENT DOCUMENTS

WO   2012/104007 A2   8/2012

OTHER PUBLICATIONS

International Search Report dated Jan. 8, 2014 issued in corresponding PCT/EP2013/002696 application (pp. 1-2).

* cited by examiner

*Primary Examiner* — Niloofar Rahmani
(74) *Attorney, Agent, or Firm* — Millen White Zelano and Branigan, PC; John Sopp; Csaba Henter

(57) ABSTRACT

The compound 4-(2-methyl-1H-pyrrolo[2,3-b]pyridin-3-yl)-2,7-naphthyridin-1-ylamine and pharmaceutically usable salts and/or tautomers thereof. The use of this compound for the treatment of tumors, tumor growth, tumor metastases and/or AIDS.

8 Claims, No Drawings

7-AZAINDOLE-2,7-NAPHTHYRIDINE DERIVATIVE FOR THE TREATMENT OF TUMOURS

The invention relates to the compound 4-(2-methyl-1H-pyrrolo[2,3-b]pyridin-3-yl)-2,7-naphthyridin-1-ylamine

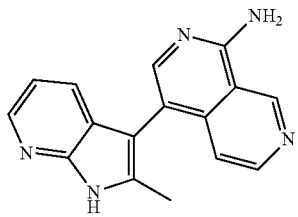 [SMILES: Cc1[nH]c2ncccc2c1-c1cnc(N)c2cnccc12]

and pharmaceutically usable salts and/or tautomers thereof.

The invention was based on the object of finding novel compounds having valuable properties, in particular those which can be used for the preparation of medicaments.

It has been found that the compound according to the invention and salts and/or tautomers thereof have very valuable pharmacological properties while being well tolerated.

In particular, it exhibits a cell proliferation/cell vitality-inhibiting action as antagonist or agonist. The compound according to the invention can therefore be used for the combating and/or treatment of tumours, tumour growth and/or tumour metastases.

The antiproliferative action can be tested in a proliferation assay/vitality assay.

Accordingly, the compound according to the invention or a pharmaceutically acceptable salt thereof is administered for the treatment of cancer, including solid carcinomas, such as, for example, carcinomas (for example of the lungs, pancreas, thyroid, bladder or colon), myeloid diseases (for example myeloid leukaemia) or adenomas (for example villous colon adenoma).

The tumours furthermore include monocytic leukaemia, brain, urogenital, lymphatic system, stomach, laryngeal and lung carcinoma, including lung adenocarcinoma and small-cell lung carcinoma, pancreatic and/or breast carcinoma.

The compound is furthermore useful in the treatment of immune deficiency induced by HIV-1 (Human Immunodeficiency Virus Type 1).

Cancer-like hyperproliferative diseases are to be regarded as brain cancer, lung cancer, squamous epithelial cancer, bladder cancer, stomach cancer, pancreatic cancer, liver cancer, renal cancer, colorectal cancer, breast cancer, head cancer, neck cancer, oesophageal cancer, gynaecological cancer, thyroid cancer, lymphomas, chronic leukaemia and acute leukaemia. In particular, cancer-like cell growth is a disease which represents a target of the present invention. The present invention therefore relates to the compound according to the invention as medicament and/or medicament active compound in the treatment and/or prophylaxis of the said diseases and to the use of compound according to the invention for the preparation of a pharmaceutical for the treatment and/or prophylaxis of the said diseases and to a method for the treatment of the said diseases comprising the administration of the compound according to the invention to a patient in need of such an administration.

It can be shown that the compound according to the invention has an antiproliferative action. The compound according to the invention is administered to a patient having a hyperproliferative disease, for example to inhibit tumour growth, to reduce inflammation associated with a lymphoproliferative disease, to inhibit transplant rejection or neurological damage due to tissue repair, etc. The present compound is useful for prophylactic or therapeutic purposes. As used herein, the term "treatment" is used to refer to both the prevention of diseases and the treatment of pre-existing conditions. The prevention of proliferation/vitality is achieved by administration of the compound according to the invention prior to the development of overt disease, for example for preventing tumour growth. Alternatively, the compound is used for the treatment of ongoing diseases by stabilising or improving the clinical symptoms of the patient.

The host or patient can belong to any mammalian species, for example a primate species, particularly humans; rodents, including mice, rats and hamsters; rabbits; horses, cows, dogs, cats, etc. Animal models are of interest for experimental investigations, providing a model for treatment of a human disease.

The susceptibility of a particular cell to treatment with the compound according to the invention can be determined by in vitro testing. Typically, a culture of the cell is incubated with the compound according to the invention at various concentrations for a period of time which is sufficient to allow the active agents to induce cell death or to inhibit cell proliferation, cell vitality or migration, usually between about one hour and one week. In vitro testing can be carried out using cultivated cells from a biopsy sample. The amount of cells remaining after the treatment are then determined.

The dose varies depending on the specific compound used, the specific disease, the patient status, etc. A therapeutic dose is typically sufficient considerably to reduce the undesired cell population in the target tissue, while the viability of the patient is maintained. The treatment is generally continued until a considerable reduction has occurred, for example an at least about 50% reduction in the cell burden, and may be continued until essentially no more undesired cells are detected in the body.

There are many diseases associated with deregulation of cell proliferation and cell death (apoptosis). The conditions of interest include, but are not limited to, the following. The compound according to the invention is useful in the treatment of various conditions where proliferation and/or migration of smooth muscle cells and/or inflammatory cells into the intimal layer of a vessel is present, resulting in restricted blood flow through that vessel, for example in the case of neointimal occlusive lesions. Occlusive graft vascular diseases of interest include atherosclerosis, coronary vascular disease after grafting, vein graft stenosis, perianastomatic prosthetic restenosis, restenosis after angioplasty or stent placement, and the like.

The compound according to the invention also acts as regulator, modulator or inhibitor of protein kinases, in particular of the serine/threonine kinase type, which include, inter alia, phosphoinositide-dependent kinase 1 (PDK1). The compound according to the invention exhibits a certain action in the inhibition of the serine/threonine kinases PDK1, IKKε and TBK1, and in the case of ALK-1.

PDK1 phosphorylates and activates a sub-group of the AGC protein kinase family, comprising PKB, SGK, S6K and PKC isoforms. These kinases are involved in the PI3K signal transduction pathway and control basic cellular functions, such as survival, growth and differentiation. PDK1 is thus an important regulator of diverse metabolic, proliferative and life-sustaining effects.

The compound according to the invention also exhibits TGFβ receptor I kinase-inhibiting properties.

A number of diseases have been associated with TGF-β1 overproduction. Inhibitors of the intracellular TGF-β signalling pathway are suitable treatments for fibroproliferative diseases. Specifically, fibroproliferative diseases include kidney disorders associated with unregulated TGF-β activity and excessive fibrosis including glomerulonephritis (GN), such as mesangial proliferative GN, immune GN and crescentic GN. Other renal conditions include diabetic nephropathy, renal interstitial fibrosis, renal fibrosis in transplant patients receiving cyclosporin, and HIV-associated nephropathy. Collagen vascular disorders include progressive systemic sclerosis, polymyositis, sclerodermatitis, dermatomyositis, eosinophilic fasciitis, morphea, or those associated with the occurrence of Raynaud's syndrome. Lung fibroses resulting from excessive TGF-β activity include adult respiratory distress syndrome, idiopathic pulmonary fibrosis, and interstitial pulmonary fibrosis often associated with autoimmune disorders, such as systemic lupus erythematosus and sclerodermatitis, chemical contact or allergies. Another autoimmune disorder associated with fibroproliferative characteristics is rheumatoid arthritis.

Eye diseases associated with a fibroproliferative condition include proliferative vitreoretinopathy occurring during retinal reattachment surgery, cataract extraction with intraocular lens implantation, and post-glaucoma drainage surgery and are associated with TGF-β1 overproduction.

TGF-β1, as member of the TGF-β family, is a ligand of the TGF-β receptor family which consists of heterodimeric proteins localised on the cell membrane which have an extracellular receptor part and an intracellular kinase domain. Members are the type I and type II receptors; see also Hinck FEBS Lett. 2012 http://dx.doi.org/10.1016/j.febslet.2012.05.028

For signal transduction of the ligands TGF-β1, -β2 and -β3 via their corresponding receptors, it is known that they play a role in cell cycle arrest in epithelial and haematopoietic cells, control of mesenchymal cell proliferation and differentiation, in wound healing, production of extracellular matrix and immune suppression, see also review by Massague Annu. Rev. Biochem. 1998. 67:753-91.

If TGF-β1 binds to a type II receptor, the corresponding type I receptor associates and is phosphorylated. This complex phosphorylates a receptor-regulated Smad protein (R-Smad), which then associates with Smad4, migrates to the cell core and leads to a change in the cell behaviour there by activation of transcription.

TGF-β type I receptor, also called ALK5 (activin receptor-like kinase 5) or TβR-I, is well documented in SwissProt under P36897, as is the type II receptor under P37173 and ALK-1 under P37023. Smad2 and Smad3 are signalling proteins for ALK-5, and those for ALK-1 are Smad-1, -5 and -8 See also Cunha BLOOD, 30 Jun. 2011 VOLUME 117, NUMBER 26, 6999

The compound according to the invention represents a selection from WO 2012/104007.

The compound according to the invention has significantly higher activity than the structurally closest compounds from WO 2012/104007.

WO 2005/095400 A1 describes other azaindole derivatives as protein kinase inhibitors.

WO 2008/079988 A2 describes quinazoline derivatives as PDK-1 inhibitors for combating cancer.

WO 2008/112217 A1 describes benzonaphthyridine derivatives as PDK1 inhibitors for combating cancer.

Pyridinonyl derivatives are known from WO 2008/005457 as PDK1 inhibitors for combating cancer.

Pyrrolopyridine kinase modulators for combating cancer are described in WO 2008/124849.

WO 2006/106326 A1 and WO 2008/156726 A1 describe other heterocyclic compounds as PDK1 inhibitors for combating cancer.

WO 2009/054941 A1 describes pyrrolopyridine derivatives as PDK1 inhibitors for combating cancer.

IKKε and TBK1 are serine/threonine kinases which are highly homologous to one another and to other IkB kinases. The two kinases play an integral role in the innate immune system. Double-stranded RNA viruses are recognised by the Toll-like receptors 3 and 4 and the RNA helicases RIG-I and MDA-5 and result in activation of the TRIF-TBK1/IKKε-IRF3 signalling cascade, which results in a type I interferon response.

In 2007, Boehm et al. described IKKε as a novel breast cancer oncogene [J. S. Boehm et al., Cell 129, 1065-1079, 2007]. 354 kinases were investigated with respect to their ability to recapitulate the Ras-transforming phenotype together with an activated form of the MAPK kinase Mek. IKKε was identified here as a cooperative oncogene.

In addition, the authors were able to show that IKBKE is amplified and overexpressed in numerous breast cancer cell lines and tumour samples. The reduction in gene expression by means of RNA interference in breast cancer cells induces apoptosis and impairs the proliferation thereof. Eddy et al. obtained similar findings in 2005, which underlines the importance of IKKε in breast cancer diseases [S. F. Eddy et al., Cancer Res. 2005; 65 (24), 11375-11383].

A protumorigenic effect of TBK1 was reported for the first time in 2006. In a screening of a gene library comprising 251,000 cDNA, Korherr et al. identified precisely three genes, TRIF, TBK1 and IRF3, which are typically involved in the innate immune defence as proangiogenic factors [C. Korherr et al., PNAS, 103, 4240-4245, 2006]. In 2006, Chien et al. [Y. Chien et al., Cell 127, 157-170, 2006] published that TBK1−/− cells can only be transformed to a limited extent using oncogenic Ras, which suggests an involvement of TBK1 in the Ras-mediated transformation. Furthermore, they were able to show that an RNAi-mediated knockdown of TBK1 triggers apoptosis in MCF-7 and Panc-1 cells. Barbie et al. recently published that TBK1 is of essential importance in numerous cancer cell lines with mutated K-Ras, which suggests that TBK1 intervention could be of therapeutic importance in corresponding tumours [D. A. Barbie et al., Nature Letters 1-5, 2009].

S. I. Cunha and K. Pietras in Blood, 117 (26), 6999-7006 (2011), describe the retardation of tumour growth by inhibition of the receptor ALK1, in particular in the case of breast carcinoma and melanoma.

Diseases caused by protein kinases are characterised by anomalous activity or hyperactivity of such protein kinases. Anomalous activity relates to either: (1) expression in cells which do not usually express these protein kinases; (2) increased kinase expression, which results in undesired cell proliferation, such as cancer; (3) increased kinase activity, which results in undesired cell proliferation, such as cancer, and/or in hyperactivity of the corresponding protein kinases. Hyperactivity relates either to amplification of the gene which encodes for a certain protein kinase, or the generation of an activity level which can be correlated with a cell proliferation disease (i.e. the severity of one or more symptoms of the cell proliferation disease increases with increasing kinase level). The bioavailability of a protein kinase may also be influenced by the presence or absence of a set of binding proteins of this kinase.

The most important types of cancer that can be treated using the compound according to the invention include colorectal cancer, small-cell lung cancer, non-small-cell lung cancer, multiple myeloma as well as renal cell carcinoma and endometrium carcinoma, particularly also types of cancer in which PTEN is mutated, inter alia breast cancer, prostate cancer and glioblastoma.

In addition, the compound according to the invention can be used to achieve additive or synergistic effects in certain existing cancer chemotherapies and radiotherapies and/or to restore the efficacy of certain existing cancer chemotherapies and radiotherapies.

The compound according to the invention is also taken to mean the hydrates and solvates of this compound, furthermore pharmaceutically usable derivatives.

The invention also relates to the salts, and the hydrates and solvates of this compound. Solvate of the compound are taken to mean adductions of inert solvent molecules onto the compounds which form owing to their mutual attractive force. Solvate are, for example, mono- or dihydrates or alcoholates.

The invention naturally also relates to the solvates of the salts of the compound according to the invention.

Pharmaceutically usable derivatives are taken to mean, for example, the salts of the compound according to the invention and also so-called prodrug compounds.

Prodrug derivative is taken to mean the compound according to the invention which has been modified by means of, for example, alkyl or acyl groups, sugars or oligopeptides and which is rapidly cleaved in the organ-ism to form the active compound according to the invention.

These also include biodegradable polymer derivatives of the compound according to the invention, as described, for example, in Int. J. Pharm. 115, 61-67 (1995).

The expression "effective amount" denotes the amount of a medicament or of a pharmaceutical active compound which causes in a tissue, system, animal or human a biological or medical response which is sought or desired, for example, by a researcher or physician.

In addition, the expression "therapeutically effective amount" denotes an amount which, compared with a corresponding subject who has not received this amount, has the following consequence:
improved treatment, healing, prevention or elimination of a disease, syndrome, condition, complaint, disorder or side effects or also the reduction in the advance of a disease, condition or disorder.

The expression "therapeutically effective amount" also encompasses the amounts which are effective for increasing normal physiological function.

The invention relates to the compound 4-(2-methyl-1H-pyrrolo[2,3-b]pyridin-3-yl)-2,7-naphthyridin-1-ylamine and salts thereof and to a process for the preparation of this compound and to pharmaceutically usable salts and tautomers thereof, characterised in that
in a Masuda reaction a compound of the formula II

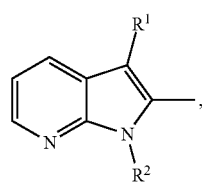

in which $R^1$ denotes Br or I and $R^2$ denotes an azaindole protecting group, is reacted with 4,4,5,5-tetramethyl-1,3,2-dioxaborolane, and the pinacolyl boronate formed as intermediate is reacted, in a Suzuki reaction, with a compound of the formula III

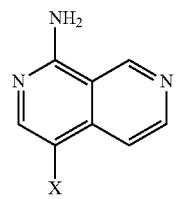

in which X denotes Cl, Br or I,
to give a compound of the formula IV

IV in which $R^2$ denotes an azaindole protecting group,
and the protecting group $R^2$ is subsequently cleaved off from the compound of the formula IV,
and/or 4-(2-methyl-1H-pyrrolo[2,3-b]pyridin-3-yl)-2,7-naphthyridin-1-ylamine is converted into one of its salts.

Above and below, the radicals $R^1$ and $R^2$ have the meanings indicated in the case of the formulae II, II and IV, unless expressly indicated otherwise.

$R^1$ denotes Br or I, preferably I.

$R^2$ denotes an azaindole protecting group, preferably tert-butyloxycarbonyl or benzenesulfonyl, particularly preferably benzenesulfonyl.

The benzenesulfonyl protecting group may also be replaced by other sulfonyl or oxycarbonyl protecting groups known to the person skilled in the art.

The cleavage of alkyl or arylsulfonyl groups is carried out using alkali metal hydroxide and primary alcohols under standard conditions.

The compound 4-(2-methyl-1H-pyrrolo[2,3-b]pyridin-3-yl)-2,7-naphthyridin-1-ylamine and also the starting materials for the preparation thereof are, in addition, prepared by methods known per se, as described in the literature (for example in the standard works, such as Houben-Weyl, Methoden der organischen Chemie [Methods of Organic Chemistry], Georg-Thieme-Verlag, Stuttgart), to be precise under reaction conditions which are known and suitable for the said reactions. Use can also be made here of variants known per se which are not mentioned here in greater detail.

The compound 4-(2-methyl-1H-pyrrolo[2,3-b]pyridin-3-yl)-2,7-naphthyridin-1-ylamine can preferably be obtained by reacting a compound of the formula II with a compound of the formula III in a sequential Masuda/Suzuki reaction.

In the compounds of the formula III, X preferably denotes Cl, Br or I.

After the reaction of the compounds of the formula II with the compounds of the formula III, the azaindole protecting group $R^2$ is also cleaved off.

The reaction is carried out under the conditions of a Suzuki coupling. Depending on the conditions used, the reaction time is between a few minutes and 14 days, the reaction temperature is between about −30° and 140°, normally between 0° and 110°, in particular between about 70° and about 100°.

Suitable inert solvents are, for example, hydrocarbons, such as hexane, petroleum ether, benzene, toluene or xylene; chlorinated hydrocarbons, such as trichloroethylene, 1,2-dichloroethane, carbon tetrachloride, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether, ethylene glycol dimethyl ether (diglyme); ketones, such as acetone or butanone; amides, such as acetamide, dimethylacetamide or dimethylformamide (DMF); nitriles, such as acetonitrile; sulfoxides, such as dimethyl sulfoxide (DMSO); carbon disulfide; carboxylic acids, such as formic acid or acetic acid; nitro compounds, such as nitromethane or nitrobenzene; esters, such as ethyl acetate, or mixtures of the said solvents.

Particular preference is given to dimethoxyethane, diglyme, methanol and/or dioxane.

Pharmaceutical Salts and Other Forms

The said compound according to the invention can be used in its final non-salt form. On the other hand, the present invention also encompasses the use of this compound in the form of pharmaceutically acceptable salts thereof, which can be derived from various organic and inorganic acids and bases by procedures known in the art. Pharmaceutically acceptable salt forms of the compound according to the invention are for the most part prepared by conventional methods. The acid-addition salts can be formed by treating the compound according to the invention with pharmaceutically acceptable organic and inorganic acids, for example hydrogen halides, such as hydrogen chloride, hydrogen bromide or hydrogen iodide, other mineral acids and corresponding salts thereof, such as sulfate, nitrate or phosphate and the like, and alkyl- and monoarylsulfonates, such as ethanesulfonate, toluenesulfonate and benzenesulfonate, and other organic acids and corresponding salts thereof, such as acetate, trifluoroacetate, tartrate, maleate, succinate, citrate, benzoate, salicylate, ascorbate and the like. Accordingly, pharmaceutically acceptable acid-addition salts of the compound according to the invention include the following: acetate, adipate, alginate, arginate, aspartate, benzoate, benzenesulfonate (besylate), bisulfate, bisulfite, bromide, butyrate, camphorate, camphorsulfonate, caprylate, chloride, chlorobenzoate, citrate, cyclopentanepropionate, digluconate, dihydrogenphosphate, dinitrobenzoate, dodecylsulfate, ethanesulfonate, fumarate, galacterate (from mucic acid), galacturonate, glucoheptanoate, gluconate, glutamate, glycerophosphate, hemisuccinate, hemisulfate, heptanoate, hexanoate, hippurate, hydrochloride, hydrobromide, hydroiodide, 2-hydroxyethanesulfonate, iodide, isethionate, isobutyrate, lactate, lactobionate, malate, maleate, malonate, mandelate, metaphosphate, methanesulfonate, methylbenzoate, monohydrogenphosphate, 2-naphthalenesulfonate, nicotinate, nitrate, oxalate, oleate, palmoate, pectinate, persulfate, phenylacetate, 3-phenylpropionate, phosphate, phosphonate, phthalate, but this does not represent a restriction.

The compound of the present invention, which contains basic nitrogen-containing groups, can be quaternised using agents such as ($C_1$-$C_4$)alkyl halides, for example methyl, ethyl, isopropyl and tert-butyl chloride, bromide and iodide; di($C_1$-$C_4$)alkyl sulfates, for example dimethyl, diethyl and diamyl sulfate; ($C_{10}$-$C_{18}$)alkyl halides, for example decyl, dodecyl, lauryl, myristyl and stearyl chloride, bromide and iodide; and aryl($C_1$-$C_4$)alkyl halides, for example benzyl chloride and phenethyl bromide. Both water- and oil-soluble compounds according to the invention can be prepared using such salts.

The above-mentioned pharmaceutical salts which are preferred include acetate, trifluoroacetate, besylate, citrate, fumarate, gluconate, hemisuccinate, hippurate, hydrochloride, hydrobromide, isethionate, mandelate, meglumine, nitrate, oleate, phosphonate, pivalate, sodium phosphate, stearate, sulfate, sulfosalicylate, tartrate, thiomalate, tosylate and tromethamine, but this is not intended to represent a restriction.

The acid-addition salts of the compound according to the invention are prepared by bringing the free base form into contact with a sufficient amount of the desired acid, causing the formation of the salt in a conventional manner. The free base can be regenerated by bringing the salt form into contact with a base and isolating the free base in a conventional manner. The free base forms differ in a certain respect from the corresponding salt forms thereof with respect to certain physical properties, such as solubility in polar solvents; for the purposes of the invention, however, the salts otherwise correspond to the respective free base forms thereof.

If a compound according to the invention contains more than one group which is capable of forming pharmaceutically acceptable salts of this type, the invention also encompasses multiple salts. Typical multiple salt forms include, for example, bitartrate, diacetate, difumarate, dimeglumine, diphosphate, disodium and trihydrochloride, but this is not intended to represent a restriction.

With regard to that stated above, it can be seen that the expression "pharmaceutically acceptable salt" in the present connection is taken to mean an active compound which comprises the compound according to the invention in the form of one of its salts, in particular if this salt form imparts improved pharmacokinetic properties on the active compound compared with the free form of the active compound or any other salt form of the active compound used earlier. The pharmaceutically acceptable salt form of the active compound can also provide this active compound for the first time with a desired pharmacokinetic property which it did not have earlier and can even have a positive influence on the pharmacodynamics of this active compound with respect to its therapeutic efficacy in the body.

The invention furthermore relates to medicaments comprising 4-(2-methyl-1H-pyrrolo[2,3-b]pyridin-3-yl)-2,7-naphthyridin-1-ylamine and/or pharmaceutically usable salts and tautomers thereof, and optionally excipients and/or adjuvants.

Pharmaceutical formulations can be administered in the form of dosage units which comprise a predetermined amount of active compound per dosage unit. Such a unit can comprise, for example, 0.5 mg to 1 g, preferably 1 mg to 700 mg, particularly preferably 5 mg to 100 mg, of the compound according to the invention, depending on the condition treated, the method of administration and the age, weight and condition of the patient, or pharmaceutical formulations can be administered in the form of dosage units which comprise a predetermined amount of active compound per dosage unit. Preferred dosage unit formulations are those which comprise a daily dose or part-dose, as indicated above, or a corresponding fraction thereof of an active compound. Furthermore, pharmaceutical formulations of this type can be prepared using a process which is generally known in the pharmaceutical art.

Pharmaceutical formulations can be adapted for administration via any desired suitable method, for example by oral (including buccal or sublingual), rectal, nasal, topical (including buccal, sublingual or transdermal), vaginal or parenteral (including subcutaneous, intramuscular, intravenous or intradermal) methods. Such formulations can be prepared using all processes known in the pharmaceutical art by, for example, combining the active compound with the excipient(s) or adjuvant(s).

Pharmaceutical formulations adapted for oral administration can be administered as separate units, such as, for example, capsules or tablets; powders or granules; solutions or suspensions in aqueous or non-aqueous liquids; edible foams or foam foods; or oil-in-water liquid emulsions or water-in-oil liquid emulsions.

Thus, for example, in the case of oral administration in the form of a tablet or capsule, the active-ingredient component can be combined with an oral, non-toxic and pharmaceutically acceptable inert excipient, such as, for example, ethanol, glycerol, water and the like. Powders are prepared by comminuting the compound to a suitable fine size and mixing it with a pharmaceutical excipient comminuted in a similar manner, such as, for example, an edible carbohydrate, such as, for example, starch or mannitol. A flavour, preservative, dispersant and dye may likewise be present.

Capsules are produced by preparing a powder mixture as described above and filling shaped gelatine shells therewith. Glidants and lubricants, such as, for example, highly disperse silicic acid, talc, magnesium stearate, calcium stearate or polyethylene glycol in solid form, can be added to the powder mixture before the filling operation. A disintegrant or solubiliser, such as, for example, agar-agar, calcium carbonate or sodium carbonate, can likewise be added in order to improve the availability of the medicament after the capsule has been taken.

In addition, if desired or necessary, suitable binders, lubricants and disintegrants as well as dyes can likewise be incorporated into the mixture. Suitable binders include starch, gelatine, natural sugars, such as, for example, glucose or beta-lactose, sweeteners made from maize, natural and synthetic rubber, such as, for example, acacia, tragacanth or sodium alginate, carboxymethylcellulose, polyethylene glycol, waxes, and the like. The lubricants used in these dosage forms include sodium oleate, sodium stearate, magnesium stearate, sodium benzoate, sodium acetate, sodium chloride and the like. The disintegrants include, without being restricted thereto, starch, methylcellulose, agar, bentonite, xanthan gum and the like. The tablets are formulated by, for example, preparing a powder mixture, granulating or dry-pressing the mixture, adding a lubricant and a disintegrant and pressing the entire mixture to give tablets. A powder mixture is prepared by mixing the compound comminuted in a suitable manner with a diluent or a base, as described above, and optionally with a binder, such as, for example, carboxymethylcellulose, an alginate, gelatine or polyvinylpyrrolidone, a dissolution retardant, such as, for example, paraffin, an absorption accelerator, such as, for example, a quaternary salt, and/or an absorbant, such as, for example, bentonite, kaolin or dicalcium phosphate. The powder mixture can be granulated by wetting it with a binder, such as, for example, syrup, starch paste, acadia mucilage or solutions of cellulose or polymer materials and pressing it through a sieve. As an alternative to granulation, the powder mixture can be run through a tableting machine, giving lumps of non-uniform shape, which are broken up to form granules. The granules can be lubricated by addition of stearic acid, a stearate salt, talc or mineral oil in order to prevent sticking to the tablet casting moulds. The lubricated mixture is then pressed to give tablets. The compound according to the invention can also be combined with a free-flowing inert excipient and then pressed directly to give tablets without carrying out the granulation or dry-pressing steps. A transparent or opaque protective layer consisting of a shellac sealing layer, a layer of sugar or polymer material and a gloss layer of wax may be present. Dyes can be added to these coatings in order to be able to differentiate between different dosage units.

Oral liquids, such as, for example, solution, syrups and elixirs, can be prepared in the form of dosage units so that a given quantity comprises a pre-specified amount of the compound. Syrups can be prepared by dissolving the compound in an aqueous solution with a suitable flavour, while elixirs are prepared using a non-toxic alcoholic vehicle. Suspensions can be formulated by dispersion of the compound in a non-toxic vehicle. Solubilisers and emulsifiers, such as, for example, ethoxylated isostearyl alcohols and polyoxyethylene sorbitol ethers, preservatives, flavour additives, such as, for example, peppermint oil or natural sweeteners or saccharin, or other artificial sweeteners and the like, can likewise be added.

The dosage unit formulations for oral administration can, if desired, be encapsulated in microcapsules. The formulation can also be prepared in such a way that the release is extended or retarded, such as, for example, by coating or embedding of particulate material in polymers, wax and the like.

The compound according to the invention and salts and tautomers thereof can also be administered in the form of liposome delivery systems, such as, for example, small unilamellar vesicles, large unilamellar vesicles and multilamellar vesicles. Liposomes can be formed from various phospholipids, such as, for example, cholesterol, stearylamine or phosphatidyl-cholines.

The compound according to the invention and salts and tautomers thereof can also be delivered using monoclonal antibodies as individual carriers to which the compound molecules are coupled. The compounds can also be coupled to soluble polymers as targeted medicament carriers. Such polymers may encompass polyvinylpyrrolidone, pyran copolymer, polyhydroxypropylmethacrylamidophenol, polyhydroxyethylaspartamidophenol or polyethylene oxide polylysine, substituted by palmitoyl radicals. The compounds may furthermore be coupled to a class of biodegradable polymers which are suitable for achieving controlled release of a medicament, for example polylactic acid, poly-epsilon-caprolactone, polyhydroxybutyric acid, polyorthoesters, polyacetals, polydihydroxypyrans, polycyanoacrylates and crosslinked or amphipathic block copolymers of hydrogels.

Pharmaceutical formulations adapted for transdermal administration can be administered as independent plasters for extended, close contact with the epidermis of the recipient. Thus, for example, the active compound can be delivered from the plaster by iontophoresis, as described in general terms in Pharmaceutical Research, 3(6), 318 (1986).

Pharmaceutical compounds adapted for topical administration can be formulated as ointments, creams, suspensions, lotions, powders, solutions, pastes, gels, sprays, aerosols or oils.

For the treatment of the eye or other external tissue, for example mouth and skin, the formulations are preferably applied as topical ointment or cream. In the case of formulation to give an ointment, the active compound can be employed either with a paraffinic or a water-miscible cream base. Alternatively, the active compound can be formulated to give a cream with an oil-in-water cream base or a water-in-oil base.

Pharmaceutical formulations adapted for topical application to the eye include eye drops, in which the active compound is dissolved or suspended in a suitable carrier, in particular an aqueous solvent.

Pharmaceutical formulations adapted for topical application in the mouth encompass lozenges, pastilles and mouthwashes.

Pharmaceutical formulations adapted for rectal administration can be administered in the form of suppositories or enemas.

Pharmaceutical formulations adapted for nasal administration in which the carrier substance is a solid comprise a coarse powder having a particle size, for example, in the range 20-500 microns, which is administered in the manner in which snuff is taken, i.e. by rapid inhalation via the nasal passages from a container containing the powder held close to the nose. Suitable formulations for administration as nasal spray or nose drops with a liquid as carrier substance encompass active-ingredient solutions in water or oil.

Pharmaceutical formulations adapted for administration by inhalation encompass finely particulate dusts or mists, which can be generated by various types of pressurised dispensers with aerosols, nebulisers or insufflators.

Pharmaceutical formulations adapted for vaginal administration can be administered as pessaries, tampons, creams, gels, pastes, foams or spray formulations.

Pharmaceutical formulations adapted for parenteral administration include aqueous and non-aqueous sterile injection solutions comprising antioxidants, buffers, bacteriostatics and solutes, by means of which the formulation is rendered isotonic with the blood of the recipient to be treated; and aqueous and non-aqueous sterile suspensions, which may comprise suspension media and thickeners. The formulations can be administered in single-dose or multidose containers, for example sealed ampoules and vials, and stored in freeze-dried (lyophilised) state, so that only the addition of the sterile carrier liquid, for example water for injection purposes, immediately before use is necessary. Injection solutions and suspensions prepared in accordance with the recipe can be prepared from sterile powders, granules and tablets.

It goes without saying that, in addition to the above particularly mentioned constituents, the formulations may also comprise other agents usual in the art with respect to the particular type of formulation; thus, for example, formulations which are suitable for oral administration may comprise flavours.

A therapeutically effective amount of the compound according to the invention depends on a number of factors, including, for example, the age and weight of the animal, the precise condition that requires treatment, and its severity, the nature of the formulation and the method of administration, and is ultimately determined by the treating doctor or vet. However, an effective amount of a compound according to the invention for the treatment of neoplastic growth, for example colon or breast carcinoma, is generally in the range from 0.1 to 100 mg/kg of body weight of the recipient (mammal) per day and particularly typically in the range from 1 to 10 mg/kg of body weight per day. Thus, the actual amount per day for an adult mammal weighing 70 kg is usually between 70 and 700 mg, where this amount can be administered as a single dose per day or usually in a series of part-doses (such as, for example, two, three, four, five or six) per day, so that the total daily dose is the same. An effective amount of a salt or tautomer thereof can be determined as the fraction of the effective amount of the compound according to the invention per se. It can be assumed that similar doses are suitable for the treatment of other conditions mentioned above.

The invention furthermore relates to medicaments comprising 4-(2-methyl-1H-pyrrolo[2,3-b]pyridin-3-yl)-2,7-naphthyridin-1-ylamine and/or pharmaceutically usable salts and tautomers thereof, and at least one further medicament active compound.

The invention also relates to a set (kit) consisting of separate packs of (a) an effective amount of 4-(2-methyl-1H-pyrrolo[2,3-b]pyridin-3-yl)-2,7-naphthyridin-1-ylamine and/or pharmaceutically usable salts thereof, and (b) an effective amount of a further medicament active compound.

The set comprises suitable containers, such as boxes, individual bottles, bags or ampoules. The set may, for example, comprise separate ampoules, each containing an effective amount of 4-(2-methyl-1H-pyrrolo[2,3-b]-pyridin-3-yl)-2,7-naphthyridin-1-ylamine and/or pharmaceutically usable salts and tautomers thereof, and an effective amount of a further medicament active compound dissolved or in lyophilised form.

Use

The present compound is suitable as pharmaceutical active compound for mammals, especially for humans, in the treatment and control of cancer diseases.

The invention furthermore relates to 4-(2-methyl-1H-pyrrolo[2,3-b]pyridin-3-yl)-2,7-naphthyridin-1-ylamine and pharmaceutically usable salts and tautomers thereof for use for the treatment of tumours, tumour growth, tumour metastases and/or AIDS.

The invention furthermore relates to 4-(2-methyl-1H-pyrrolo[2,3-b]pyridin-3-yl)-2,7-naphthyridin-1-ylamine and pharmaceutically usable salts and tautomers thereof, for use for the treatment of fibrosis, restenosis, HIV infection, Alzheimer's, atherosclerosis and/or for the promotion of wound healing.

The present invention encompasses the use of 4-(2-methyl-1H-pyrrolo-[2,3-b]pyridin-3-yl)-2,7-naphthyridin-1-ylamine and/or physiologically acceptable salts and tautomers thereof for the preparation of a medicament for the treatment or prevention of cancer. Preferred carcinomas for the treatment originate from the group cerebral carcinoma, urogenital tract carcinoma, carcinoma of the lymphatic system, stomach carcinoma, laryngeal carcinoma and lung carcinoma bowel cancer. A further group of preferred forms of cancer are monocytic leukaemia, lung adenocarcinoma, small-cell lung carcinomas, pancreatic cancer, glioblastomas and breast carcinoma.

Also encompassed is the use of 4-(2-methyl-1H-pyrrolo[2,3-b]pyridin-3-yl)-2,7-naphthyridin-1-ylamine and/or physiologically acceptable salts and tautomers thereof for the preparation of a medicament for the treatment and/or control of a tumour-induced disease in a mammal, in which to this method a therapeutically effective amount of a compound according to the invention is administered to a sick mammal in need of such treatment. The therapeutic amount varies according to the particular disease and can be determined by the person skilled in the art without undue effort.

Particular preference is given to the use for the treatment of a disease, where the disease is a solid tumour.

The solid tumour is preferably selected from the group of tumours of the squamous epithelium, the bladder, the stomach, the kidneys, of head and neck, the oesophagus, the cervix, the thyroid, the intestine, the liver, the brain, the prostate, the urogenital tract, the lymphatic system, the stomach, the larynx and/or the lung.

The solid tumour is furthermore preferably selected from the group lung adenocarcinoma, small-cell lung carcinomas, pancreatic cancer, glioblastomas, colon carcinoma and breast carcinoma.

Preference is furthermore given to the use for the treatment of a tumour of the blood and immune system, preferably for the treatment of a tumour selected from the group of acute myeloid leukaemia, chronic myeloid leukaemia, acute lymphatic leukaemia and/or chronic lymphatic leukaemia.

The invention furthermore relates to the use of the compound according to the invention for the treatment of bone pathologies, where the bone pathology originates from the group osteosarcoma, osteoarthritis and rickets.

4-(2-Methyl-1H-pyrrolo[2,3-b]pyridin-3-yl)-2,7-naphthyridin-1-ylamine may also be administered together with other well-known therapeutic agents that are selected for their particular usefulness against the condition that is being treated.

The present compound is also suitable for combination with known anti-cancer agents. These known anti-cancer agents include the following: oestrogen receptor modulators, androgen receptor modulators, retinoid receptor modulators, cytotoxic agents, antiproliferative agents, prenyl-protein transferase inhibitors, HMG-CoA reductase inhibitors, HIV protease inhibitors, reverse transcriptase inhibitors and further angiogenesis inhibitors. The present compounds are particularly suitable for administration at the same time as radiotherapy.

"Oestrogen receptor modulators" refers to compounds which interfere with or inhibit the binding of oestrogen to the receptor, regardless of mechanism. Examples of oestrogen receptor modulators include, but are not limited to, tamoxifen, raloxifene, idoxifene, LY353381, LY 117081, toremifene, fulvestrant, 4-[7-(2,2-dimethyl-1-oxopropoxy-4-methyl-2-[4-[2-(1-piperidinyl)-ethoxy]phenyl]-2H-1-benzopyran-3-yl]phenyl 2,2-dimethylpropanoate, 4,4'-dihydroxybenzophenone-2,4-dinitrophenylhydrazone and SH646.

"Androgen receptor modulators" refers to compounds which interfere with or inhibit the binding of androgens to the receptor, regardless of mechanism. Examples of androgen receptor modulators include finasteride and other 5α-reductase inhibitors, nilutamide, flutamide, bicalutamide, liarozole and abiraterone acetate.

"Retinoid receptor modulators" refers to compounds which interfere with or inhibit the binding of retinoids to the receptor, regardless of mechanism. Examples of such retinoid receptor modulators include bexarotene, tretinoin, 13-cis-retinoic acid, 9-cis-retinoic acid, α-difluoromethylornithine, ILX23-7553, trans-N-(4'-hydroxyphenyl)retinamide and N-4-carboxyphenyl-retinamide.

"Cytotoxic agents" refers to compounds which result in cell death primarily through direct action on the cellular function or inhibit or interfere with cell myosis, including alkylating agents, tumour necrosis factors, intercalators, microtubulin inhibitors and topoisomerase inhibitors.

Examples of cytotoxic agents include, but are not limited to, tirapazimine, sertenef, cachectin, ifosfamide, tasonermin, lonidamine, carboplatin, altretamine, prednimustine, dibromodulcitol, ranimustine, fotemustine, nedaplatin, oxaliplatin, temozolomide, heptaplatin, estramustine, improsulfan tosylate, trofosfamide, nimustine, dibrospidium chloride, pumitepa, lobaplatin, satraplatin, profiromycin, cisplatin, irofulven, dexifosfamide, cis-aminedichloro(2-methylpyridine)platinum, benzylguanine, glufosfamide, GPX100, (trans,trans,trans)bis-mu-(hexane-1,6-diamine)-mu-[di-amine-platinum(II)]bis[diamine(chloro)platinum(II)]tetrachloride, diarisidinylspermine, arsenic trioxide, 1-(11-dodecylamino-10-hydroxyundecyl)-3,7-di-methylxanthine, zorubicin, idarubicin, daunorubicin, bisantrene, mitoxantrone, pirarubicin, pinafide, valrubicin, amrubicin, antineoplaston, 3'-deamino-3'-morpholino-13-deoxo-10-hydroxycarminomycin, annamycin, galarubicin, elinafide, MEN10755 and 4-demethoxy-3-deamino-3-aziridinyl-4-methylsulfonyldaunorubicin (see WO 00/50032).

Examples of microtubulin inhibitors include paclitaxel, vindesine sulfate, 3',4'-didehydro-4'-deoxy-8'-norvincaleukoblastine, docetaxol, rhizoxin, dolastatin, mivobulin isethionate, auristatin, cemadotin, RPR109881, BMS184476, vinflunine, cryptophycin, 2,3,4,5,6-pentafluoro-N-(3-fluoro-4-methoxyphenyl)benzenesulfonamide, anhydrovinblastine, N,N-dimethyl-L-valyl-L-valyl-N-methyl-L-valyl-L-prolyl-L-proline-t-butylamide, TDX258 and BMS188797.

Topoisomerase inhibitors are, for example, topotecan, hycaptamine, irinotecan, rubitecan, 6-ethoxypropionyl-3',4'-O-exobenzylidenechartreusin, 9-methoxy-N,N-dimethyl-5-nitropyrazolo[3,4,5-kl]acridine-2-(6H)propan-amine, 1-amino-9-ethyl-5-fluoro-2,3-dihydro-9-hydroxy-4-methyl-1H,12H-benzo[de]pyrano[3',4':b,7]indolizino[1,2b]quinoline-10,13(9H,15H)-dione, lurtotecan, 7-[2-(N-isopropylamino)ethyl]-(20S)camptothecin, BNP1350, BNP|1100, BN80915, BN80942, etoposide phosphate, teniposide, sobuzoxane, 2'-dimethylamino-2'-deoxyetoposide, GL331, N-[2-(dimethylamino)-ethyl]-9-hydroxy-5,6-dimethyl-6H-pyrido[4,3-b]carbazole-1-carboxamide, asulacrine, (5a,5aB,8aa, 9b)-9-[2-[N-[2-(dimethylamino)ethyl]-N-methylamino] ethyl]-5-[4-hydroxy-3,5-dimethoxyphenyl]-5,5a,6,8,8a,9-hexahydrofuro(3',4':6,7)naphtho(2,3-d)-1,3-dioxol-6-one, 2,3-(methylenedioxy)-5-methyl-7-hydroxy-8-methoxy-benzo[c]phenanthridinium, 6,9-bis[(2-amino-ethyl)amino] benzo[g]isoquinoline-5,10-dione, 5-(3-aminopropylamino)-7,10-dihydroxy-2-(2-hydroxyethylaminomethyl)-6H-pyrazolo[4,5,1-de]acridin-6-one, N-[1-[2(diethylamino) ethylamino]-7-methoxy-9-oxo-9H-thioxanthen-4-ylmethyl] formamide, N-(2-(dimethylamino)ethyl)acridine-4-carboxamide, 6-[[2-(dimethylamino)ethyl]amino]-3-hydroxy-7H-indeno[2,1-c]quinolin-7-one and dimesna.

"Antiproliferative agents" include antisense RNA and DNA oligonucleotides such as G3139, ODN698, RVASK-RAS, GEM231 and INX3001 and anti-metabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoromethylene-2'-deoxycytidine, N-[5-(2,3-dihydrobenzofuryl)sulfonyl]-N'-(3,4-dichlorophenyl)urea, N6-[4-deoxy-4-[N2-[2(E),4(E)-tetradecadienoyl]glycylamino]-L-glycero-B-L-mannohepto-pyranosyl]adenine, aplidine, ecteinascidin, troxacitabine, 4-[2-amino-4-oxo-4,6,7,8-tetrahydro-3H-pyrimidino[5,4-b]-1,4-thiazin-6-yl-(S)-ethyl]-2,5-thienoyl-L-glutamic acid, aminopterin, 5-fluorouracil, alanosine, 11-acetyl-8-(carbamoyloxymethyl)-4-formyl-6-methoxy-14-oxa-1,11-diazatetracyclo-(7.4.1.0.0)tetradeca-2,4,6-trien-9-ylacetic acid ester, swainsonine, lometrexol, dexrazoxane, methioninase, 2'-cyano-2'-deoxy-N4-palmitoyl-1-B-D-arabinofuranosyl cytosine and 3-aminopyridine-2-carboxaldehyde thiosemicarbazone. "Antiproliferative agents" also include monoclonal antibodies to growth factors other than those listed under "angiogenesis inhibitors", such as trastuzumab, and tumour suppressor genes, such as p53, which can be delivered via recombinant virus-mediated gene transfer (see U.S. Pat. No. 6,069,134, for example).

The medicaments of the following table are preferably, but not exclusively, combined with 4-(2-methyl-1H-pyrrolo[2,3-b]pyridin-3-yl)-[2,7]naphthyridin-1-ylamin.

TABLE 1

| | | |
|---|---|---|
| Alkylating agents | Cyclophosphamide | Lomustine |
| | Busulfan | Procarbazine |
| | Ifosfamide | Altretamine |
| | Melphalan | Estramustine phosphate |
| | Hexamethylmelamine | Mechloroethamine |
| | Thiotepa | Streptozocin |
| | chloroambucil | Temozolomide |
| | Dacarbazine | Semustine |
| | Carmustine | |
| Platinum agents | Cisplatin | Carboplatin |
| | Oxaliplatin | ZD-0473 (AnorMED) |
| | Spiroplatin | Lobaplatin (Aeterna) |
| | Carboxyphthalatoplatinum | Satraplatin (Johnson Matthey) |
| | Tetraplatin | BBR-3464 |
| | Ormiplatin | (Hoffmann-La Roche) |
| | Iproplatin | SM-11355 (Sumitomo) |
| | | AP-5280 (Access) |
| Antimetabolites | Azacytidine | Tomudex |
| | Gemcitabine | Trimetrexate |
| | Capecitabine | Deoxycoformycin |
| | 5-fluorouracil | Fludarabine |
| | Floxuridine | Pentostatin |
| | 2-chlorodesoxyadenosine | Raltitrexed |
| | 6-Mercaptopurine | Hydroxyurea |
| | 6-Thioguanine | Decitabine (SuperGen) |
| | Cytarabine | Clofarabine (Bioenvision) |
| | 2-fluorodesoxycytidine | Irofulven (MGI Pharma) |
| | Methotrexate | DMDC (Hoffmann-La Roche) |
| | Idatrexate | Ethynylcytidine (Taiho) |
| Topoisomerase inhibitors | Amsacrine | Rubitecan (SuperGen) |
| | Epirubicin | Exatecan mesylate (Daiichi) |
| | Etoposide | |
| | Teniposide or mitoxantrone | Quinamed (ChemGenex) |
| | | Gimatecan (Sigma-Tau) |
| | Irinotecan (CPT-11) | Diflomotecan (Beaufour-Ipsen) |
| | 7-Ethyl-10-hydroxycamptothecin | TAS-103 (Taiho) |
| | Topotecan | Elsamitrucin (Spectrum) |
| | Dexrazoxanet (TopoTarget) | J-107088 (Merck & Co) |
| | | BNP-1350 (BioNumerik) |
| | Pixantrone (Novuspharrna) | CKD-602 (Chong Kun Dang) |
| | Rebeccamycin analogue (Exelixis) | KW-2170 (Kyowa Hakko) |
| | BBR-3576 (Novuspharrna) | |
| Antitumour antibiotics | Dactinomycin (Actinomycin D | Amonafide |
| | | Azonafide |
| | Doxorubicin (Adriamycin) | Anthrapyrazole |
| | Deoxyrubicin | Oxantrazole |
| | Valrubicin | Losoxantrone |
| | Daunorubicin (Daunomycin) | Bleomycin sulfate (Blenoxan) |
| | Epirubicin | Bleomycinic acid |
| | Therarubicin | Bleomycin A |
| | Idarubicin | Bleomycin B |
| | Rubidazon | Mitomycin C |
| | Plicamycinp | MEN-10755 (Menarini) |
| | Porfiromycin | GPX-100 (Gem Pharmaceuticals) |
| | Cyanomorpholinodoxo-rubicin | |
| | Mitoxantron (Novantron) | |
| Antimitotic agents | Paclitaxel | SB 408075 (GlaxoSmithKline) |
| | Docetaxel | |
| | Colchicine | E7010 (Abbott) |
| | Vinblastine | PG-TXL (Cell Therapeutics) |
| | Vincristine | |
| | Vinorelbine | IDN 5109 (Bayer) |
| | Vindesine | A 105972 (Abbott) |
| | Dolastatin 10 (NCI) | A 204197 (Abbott) |
| | Rhizoxin (Fujisawa) | LU 223651 (BASF) |
| | Mivobulin (Warner-Lambert) | D 24851 (ASTA Medica) |
| | | ER-86526 (Eisai) |
| | Cemadotin (BASF) | Combretastatin A4 (BMS) |
| | RPR 109881A (Aventis) | Isohomohalichondrin-B |

TABLE 1-continued

| | | |
|---|---|---|
| | TXD 258 (Aventis) | (PharmaMar) |
| | Epothilone B (Novartis) | ZD 6126 (AstraZeneca) |
| | T 900607 (Tularik) | PEG-Paclitaxel (Enzon) |
| | T 138067 (Tularik) | AZ10992 (Asahi) |
| | Cryptophycin 52 (Eli Lilly) | !DN-5109 (Indena) |
| | Vinflunine (Fabre) | AVLB (Prescient |
| | Auristatin PE (Teikoku Hormone) | NeuroPharma) |
| | BMS 247550 (BMS) | Azaepothilon B (BMS) |
| | BMS 184476 (BMS) | BNP- 7787 (BioNumerik) |
| | BMS 188797 (BMS) | CA-4-prodrug (OXiGENE) |
| | Taxoprexin (Protarga) | Dolastatin-10 (NrH) |
| | | CA-4 (OXiGENE) |
| Aromatase inhibitors | Aminoglutethimide | Exemestan |
| | Letrozole | Atamestan (BioMedicines) |
| | Anastrazole | YM-511 (Yamanouchi) |
| | Formestan | |
| Thymidylate synthase inhibitors | Pemetrexed (Eli Lilly) | Nolatrexed (Eximias) |
| | ZD-9331 (BTG) | CoFactor ™ (BioKeys) |
| DNA antagonists | Trabectedin (PharmaMar) | Mafosfamide (Baxter International) |
| | Glufosfamide (Baxter International) | Apaziquone (Spectrum Pharmaceuticals) |
| | Albumin + 32P (Isotope Solutions) | O6-benzylguanine (Paligent) |
| | Thymectacin (NewBiotics) | |
| | Edotreotid (Novartis) | |
| Farnesyl transferase inhibitors | Arglabin (NuOncology Labs) | Tipifarnib (Johnson & Johnson) |
| | Ionafarnib (Schering-Plough) | Perillyl alcohol (DOR BioPharma) |
| | BAY-43-9006 (Bayer) | |
| Pump inhibitors | CBT-1 (CBA Pharma) | Zosuquidar trihydrochloride (Eli Lilly) |
| | Tariquidar (Xenova) | Biricodar dicitrate (Vertex) |
| | MS-209 (Schering AG) | |
| Histone acetyltransferase inhibitors | Tacedinaline (Pfizer) | Pivaloyloxymethyl butyrate (Titan) |
| | SAHA (Aton Pharma) | Depsipeptide (Fujisawa) |
| | MS-275 (Schering AG) | |
| Metalloproteinase inhibitors | Neovastat (Aeterna Laboratories) | CMT -3 (CollaGenex) |
| | | BMS-275291 (Celltech) |
| Ribonucleoside reductase inhibitors | Marimastat (British Biotech) | Tezacitabine (Aventis) |
| | Gallium maltolate (Titan) | Didox (Molecules for Health) |
| | Triapin (Vion) | |
| TNF-alpha agonists/ antagonists | Virulizin (Lorus Therapeutics) | Revimid (Celgene) |
| | CDC-394 (Celgene) | |
| Endothelin-A receptor antagonists | Atrasentan (Abbot) | YM-598 (Yamanouchi) |
| | ZD-4054 (AstraZeneca) | |
| Retinoic acid receptor agonists | Fenretinide (Johnson & Johnson) | Alitretinoin (Ligand) |
| | LGD-1550 (Ligand) | |
| Immunomodulators | Interferon | Dexosome therapy (Anosys) |
| | Oncophage (Antigenics) | Pentrix (Australian Cancer Technology) |
| | GMK (Progenics) | JSF-154 (Tragen) |
| | Adenocarcinoma vaccine (Biomira) | Cancer vaccine (Intercell) |
| | CTP-37 (AVI BioPharma) | Norelin (Biostar) |
| | JRX-2 (Immuno-Rx) | BLP-25 (Biomira) |
| | PEP-005 (Peplin Biotech) | MGV (Progenics) |
| | Synchrovax vaccines (CTL Immuno) | !3-Alethin (Dovetail) |
| | Melanoma vaccine (CTL Immuno) | CLL-Thera (Vasogen) |
| | p21-RAS vaccine (GemVax) | |
| Hormonal and antihormonal agents | Oestrogens | Prednisone |
| | Conjugated oestrogens | Methylprednisolone |
| | Ethynyloestradiol | Prednisolone |
| | chlorotrianisene | Aminoglutethimide |
| | Idenestrol | Leuprolide |
| | Hydroxyprogesterone caproate | Goserelin |
| | | Leuporelin |
| | Medroxyprogesterone | Bicalutamide |
| | Testosterone | Flutamide |
| | Testosterone propionate | Octreotide |
| | Fluoxymesterone | Nilutamide |
| | Methyltestosterone | Mitotan |
| | Diethylstilbestrol | P-04 (Novogen) |
| | Megestrol | 2-Methoxyoestradiol (EntreMed) |
| | Tamoxifen | |

TABLE 1-continued

| | | |
|---|---|---|
| | Toremofin | Arzoxifen (Eli Lilly) |
| | Dexamethasone | |
| Photodynamic agents | Talaporfin (Light Sciences) | Pd-Bacteriopheophorbide (Yeda) |
| | Theralux (Theratechnologies) | Lutetium-Texaphyrin (Pharmacyclics) |
| | Motexafin-Gadolinium (Pharmacyclics) | Hypericin |
| Tyrosine kinase inhibitors | Imatinib (Novartis) | Kahalide F (PharmaMar) |
| | Leflunomide (Sugen/Pharmacia) | CEP-701 (Cephalon) |
| | ZD1839 (AstraZeneca) | CEP-751 (Cephalon) |
| | Erlotinib (Oncogene Science) | MLN518 (Millenium) |
| | Canertjnib (Pfizer) | PKC412 (Novartis) |
| | Squalamine (Genaera) | Phenoxodiol O |
| | SU5416 (Pharmacia) | Trastuzumab (Genentech) |
| | SU6668 (Pharmacia) | C225 (ImClone) |
| | ZD4190 (AstraZeneca) | rhu-Mab (Genentech) |
| | ZD6474 (AstraZeneca) | MDX-H210 (Medarex) |
| | Vatalanib (Novartis) | 2C4 (Genentech) |
| | PKI166 (Novartis) | MDX-447 (Medarex) |
| | GW2016 (GlaxoSmithKline) | ABX-EGF (Abgenix) |
| | EKB-509 (Wyeth) | IMC-1C11 (ImClone) |
| | EKB-569 (Wyeth) | |
| Various agents | SR-27897 (CCK-A inhibitor, Sanofi-Synthelabo) | BCX-1777 (PNP inhibitor, BioCryst) |
| | Tocladesine (cyclic AMP agonist, Ribapharm) | Ranpirnase (ribonuclease stimulant, Alfacell) |
| | Alvocidib (CDK inhibitor, Aventis) | Galarubicin (RNA synthesis inhibitor, Dong-A) |
| | CV-247 (COX-2 inhibitor, Ivy Medical) | Tirapazamine (reducing agent, SRI International) |
| | P54 (COX-2 inhibitor, Phytopharm) | N-Acetylcysteine (reducing agent, Zambon) |
| | CapCell ™ (CYP450 stimulant, Bavarian Nordic) | R-Flurbiprofen (NF-kappaB inhibitor, Encore) |
| | GCS-IOO (gal3 antagonist, GlycoGenesys) | 3CPA (NF-kappaB inhibitor, Active Biotech) |
| | G17DT immunogen (gastrin inhibitor, Aphton) | Seocalcitol (vitamin D receptor agonist, Leo) |
| | Efaproxiral (oxygenator, Allos Therapeutics) | 131-I-TM-601 (DNA antagonist, TransMolecular) |
| | PI-88 (heparanase inhibitor, Progen) | Eflornithin (ODC inhibitor, ILEX Oncology) |
| | Tesmilifen (histamine antagonist, YM BioSciences) | Minodronic acid (osteoclast inhibitor, Yamanouchi) |
| | Histamine (histamine H2 receptor agonist, Maxim) | Indisulam (p53 stimulant, Eisai) |
| | Tiazofurin (IMPDH inhibitor, Ribapharm) | |
| | Cilengitide (integrin antagonist, Merck KGaA) | Aplidine (PPT inhibitor, PharmaMar) |
| | SR-31747 (IL-1 antagonist, Sanofi-Synthelabo) | Rituximab (CD20 antibody, Genentech) |
| | CCI-779 (mTOR kinase inhibitor, Wyeth) | Gemtuzumab (CD33 antibody, Wyeth Ayerst) |
| | Exisulind (PDE-V inhibitor, Cell Pathways) | PG2 (haematopoiesis promoter, Pharmagenesis) |
| | CP-461 (PDE-V inhibitor, Cell Pathways) | Immunol ™ (triclosan mouthwash, Endo) |
| | AG-2037 (GART inhibitor, Pfizer) | Triacetyluridine (uridine prodrug, Wellstat) |
| | WX-UK1 (plasminogen activator inhibitor, Wilex) | SN-4071 (sarcoma agent, Signature BioScience) |
| | PBI-1402 (PMN stimulant, ProMetic LifeSciences) | TransMID-107 ™ (immunotoxin, KS Biomedix) |
| | Bortezomib (proteasome inhibitor, Millennium) | PCK-3145 (apoptosis promoter, Procyon) |
| | SRL-172 (T-cell stimulant, SR Pharma) | Doranidazole (apoptosis promoter, Pola) |
| | TLK-286 (glutathione-S transferase inhibitor, Telik) | CHS-828 (cytotoxic agent, Leo) |
| | PT-100 (growth factor agonist, Point Therapeutics) | trans-Retinic acid (differentiator, NIH) |
| | Midostaurin (PKC inhibitor, Novartis) | MX6 (apoptosis promoter, MAXIA) |
| | Bryostatin-1 (PKC stimulant, GPC Biotech) | Apomine (apoptosis promoter, ILEX Oncology) |

TABLE 1-continued

| | |
|---|---|
| CDA-II (apoptosis promoter, Everlife) | Urocidine (apoptosis promoter, Bioniche) |
| SDX-101 (apoptosis promoter, Salmedix) | Ro-31-7453 (apoptosis promoter, La Roche) |
| Ceflatonin (apoptosis promoter, ChemGenex) | Brostallicin (apoptosis promoter, Pharmacia) |

4-(2-Methyl-1H-pyrrolo[2,3-b]pyridin-3-yl)-2,7-naphthyridin-1-ylamine and pharmaceutically usable salts and/or tautomers thereof is particularly preferably combined with immune modulators, preferably with anti-PDL-1 or IL-12.

The invention furthermore relates to 4-(2-methyl-1H-pyrrolo[2,3-b]pyridin-3-yl)-2,7-naphthyridin-1-ylamine and/or physiologically acceptable salts and tautomers thereof for use for the treatment of tumours, where a therapeutically effective amount of a compound of the formula I is administered in combination with a compound from the group of the immune modulators.

The invention furthermore relates to 4-(2-methyl-1H-pyrrolo[2,3-b]pyridin-3-yl)-2,7-naphthyridin-1-ylamine and/or physiologically acceptable salts and tautomers thereof for use for the treatment of tumours, where a therapeutically effective amount of a compound of the formula I is administered in combination with radiotherapy and a compound from the group of the immune modulators.

Evidence of the Action of Pharmacological Inhibitors on the Proliferation/Vitality of Tumour Cells In Vitro 1.0 Background In the present experiment description, the inhibition of tumour cell proliferation/tumour cell vitality by active compounds is described.

The cells are sown in a suitable cell density in microtitre plates (96-well format) and the test substances are added in the form of a concentration series. After four further days of cultivation in serum-containing medium, the tumour cell proliferation/tumour cell vitality can be determined by means of an Alamar Blue test system.

2.0 Experimental Procedure 2.1 Cell Culture

For example commercially available colon carcinoma cell lines, ovary cell lines, prostate cell lines or breast cell lines, etc.

The cells are cultivated in medium. At intervals of several days, the cells are detached from the culture dishes with the aid of trypsin solution and sown in suitable dilution in fresh medium. The cells are cultivated at 37° Celsius and 10% $CO_2$.

2.2. Sowing of the Cells

A defined number of cells (for example 2000 cells) per culture/well in a volume of 180 μl of culture medium are sown in microtitre plates (96 well cell-culture plates) using a multichannel pipette. The cells are subsequently cultivated in a CO2 incubator (37° C. and 10% CO2).

2.3. Addition of the Test Substances

The test substances are dissolved, for example, in DMSO and subsequently employed in corresponding concentration (if desired in a dilution series) in the cell culture medium. The dilution steps can be adapted depending on the efficiency of the active compounds and the desired spread of the concentrations. Cell culture medium is added to the test substances in corresponding concentrations. The addition of the test substances to the cells can take place on the same day as the sowing of the cells. To this end, in each case 20 μl of substance solution from the predilution plate are added to the cultures/wells. The cells are cultivated for a further 4 days at 37° Celsius and 10% $CO_2$.

2.4. Measurement of the Colour Reaction

In each case, 20 μl of Alamar Blue reagent are added per well, and the microtitre plates are incubated, for example, for a further seven hours in a CO2 incubator (at 37° C. and 10% CO2). The plates are measured in a reader with a fluorescence filter at a wavelength of 540 nm. The plates can be shaken gently immediately before the measurement.

3. Evaluation

The absorbance value of the medium control (no cells and test substances used) is subtracted from all other absorbance values. The controls (cells without test substance) are set equal to 100 percent, and all other absorbance values are set in relation thereto (for example in % of control):

Calculation:

$IC_{50}$ values (50% inhibition) are determined with the aid of statistics programs, such as, for example, RS1.

$$\frac{100 * (\text{value with cells and test substance} - \text{value of medium control})}{(\text{value with cells} - \text{value of medium control})}$$

4.0 Test for the Inhibition of PDK1

The experimental batches are carried out in a flashplate system with 384 wells/microtitration plate.

In each case, the PDK1 sample $His_6$-PDK1 (1-50) (3.4 nM), the PDK1 substrate biotin-bA-bA-KTFCGTPEYLA-PEVRREPRILSEEEQEMFRDFDYIADWC (400 nM), 4 μM ATP (with 0.2 μCi of $^{33}$P-ATP/well) and the test substance in 50 μl of conventional experimental solution per well are incubated at 30° C. for 60 min. The test substances are employed in corresponding concentrations (if desired in a dilution series). The control is carried out without test substance. The reaction is stopped using standard methods and washed. The activity of the kinase is measured via the incorporated radioactivity in top count. In order to determine the non-specific kinase reaction (blank value), the experimental batches are carried out in the presence of 100 nM staurosporine.

5.0 Evaluation

The radioactivity (decompositions per minute) of the blank value (no use of test substance in the presence of staurosporine) is subtracted from all other radioactivity values. The controls (kinase activity without test substance) are set equal to 100 percent and all other radioactivity values (after subtracting the blank value) are expressed set in relation thereto (for example in % of the control).

Calculation:

$$\frac{100 * (\text{value of the kinase activity with test substance} - \text{blank value})}{(\text{value of the control} - \text{blank value})} = \% \text{ of the control}$$

$IC_{50}$ values (50% inhibition) are determined with the aid of statistics programmes, such as, for example, RS1. $IC_{50}$ data of compounds according to the invention are indicated in Table 1.

| Material | Order No. | Manufacturer |
| --- | --- | --- |
| Microtitre plates for cell culture (Nunclon Surface 96-well plate) | 167008 | Nunc |
| DMEM | P04-03550 | Pan Biotech |
| PBS (10x) Dulbecco | 14200-067 | Gibco |
| 96-well plates (polypropylene) | 267334 | Nunc |
| AlamarBlue ™ | BUF012B | Serotec |
| FCS | 1302 | Pan Biotech GmbH |
| Trypsin/EDTA solution 10x | L 2153 | Biochrom AG |
| 75 cm² culture bottles | 353136 | BD Falcon |
| A2780 | 93112519 | ECACC |
| Colo205 | CCL222 | ATCC |
| MCF7 | HTB22 | ATCC |
| PC3 | CRL-1435 | ATCC |
| 384-well flash plates | SMP410A001PK | Perkin Elmer |

APCI-MS (atmospheric pressure chemical ionisation-mass spectrometry) $(M+H)^+$.

$IC_{50}$ data of compounds according to the invention are indicated in Table 1.

IKKε—Kinase Test (IKKepsilon)

The kinase assay is performed as 384-well flashplate assay. 1 nM IKKε, 800 nM biotinylated IκBα (19-42) peptide (biotin-C6-C6-GLKKERLLDDRHDSGLDSMKDEE) and 10 µM ATP (with 0.3 µCi of $^{33}$P-ATP/well) are incubated in a total volume of 50 µl (10 mM MOPS, 10 mM magnesium acetate, 0.1 mM EGTA, 1 mM dithiothreitol, 0.02% of Brij35, 0.1% of BSA, 0.1% of BioStab, pH 7.5) with or without test substance at 30° C. for 120 min. The reaction is stopped using 25 µl of 200 mM EDTA solution, filtered off with suction after 30 min at room temperature, and the wells are washed 3 times with 100 µl of 0.9% NaCl solution. The non-specific proportion of the kinase reaction (blank) is determined using 3 µM EMD 1126352 (BX-795). Radioactivity is measured in the Topcount. $IC_{50}$ values are calculated using RS1.

TBK1—Kinase Test

The kinase assay is performed as 384-well flashplate assay.

0.6 nM TANK binding kinase (TBK1), 800 nM biotinylated MELK-derived peptide (biotin-Ah-Ah-AKP-KGNKDYHLQTCCGSLAYRRR) and 10 µM ATP (with 0.25 µCi of $^{33}$P-ATP/well) are incubated in a total volume of 50 µl (10 mM MOPS, 10 mM magnesium acetate, 0.1 mM EGTA, 1 mM DTT, 0.02% of Brij35, 0.1% of BSA, pH 7.5) with or without test substance at 30° C. for 120 min. The reaction is stopped using 25 µl of 200 mM EDTA solution, filtered off with suction after 30 min at room temperature, and the wells are washed 3 times with 100 µl of 0.9% NaCl solution. The non-specific proportion of the kinase reaction (blank) is determined using 100 nM staurosporine. Radioactivity is measured in the Topcount. $IC_{50}$ values are calculated using RS1.

In-Vitro (Enzyme) Assay for Determination of the Efficacy of the Inhibitors of the Inhibition of TGF-Beta-Mediated Effects As an example, the ability of the inhibitors to eliminate TGF-beta-mediated growth inhibition is tested.

Cells of the lung epithelial cell line Mv1Lu are sown in a defined cell density in a 96-well microtitre plate and cultivated overnight under standard conditions. Next day, the medium is replaced by medium which comprises 0.5% of FCS and 1 ng/ml of TGF-beta, and the test substances are added in defined concentrations, generally in the form of dilution series with 5-fold steps. The concentration of the solvent DMSO is constant at 0.5%. After a further two days, Crystal Violet staining of the cells is carried out. After extraction of the Crystal Violet from the fixed cells, the absorption is measured spectrophotometrically at 550 nm. It can be used as a quantitative measure of the adherent cells present and thus of the cell proliferation during the culture.

Test for the Inhibition of ALK-5

The experimental batches are carried out in a flashplate system with 384 wells/microtitre plate.

In each case, 31.2 nM of GST-ALK5, 439 nM of GST-SMAD2 and 3 mM of ATP (with 0.3 µCi of 33P-ATP/well) in a total volume of 35 µl of buffer (20 mM HEPES, 10 mM MgCl2, 5 mM MnCl2, 1 mM DTT, 0.1% of BSA, pH 7.4) per well are incubated without or with test substance at 5 to 10 different concentrations at 30 C for 45 min. The reaction is stopped using 25 µl of 200 mM EDTA solution and filtered off with suction after 30 min at room temperature.

The wells are washed 3 times with 100 µl of 0.9% aqueous NaCl solution, and the residual radioactivity is measured in a TopCount instrument (Perkin-Elmer). The IC50 values are calculated using the RS1 software.

Evaluation

The radioactivity (decompositions per minute) of the blank value (no use of test substance in the presence of 100 nM staurosporine) is subtracted from all other radioactivity values. The controls (kinase activity without test substance) are set equal to 100 percent and all other radioactivity values (after subtracting the blank value) are expressed set in relation thereto (for example in % of the control).

Calculation:

$$\frac{100 * (\text{value of the kinase activity with test substance} - \text{blank value})}{(\text{value of the control} - \text{blank value})} = \% \text{ of the control}$$

$IC_{50}$ values (concentration of the test substance at 50% inhibition) are determined with the aid of statistics programmes, such as, for example, RS1. $IC_{50}$ data of compounds according to the invention are indicated in Table 2.

Test for the Inhibition of ALK-1

ALK1/ACVRL1

(Serine/threonine-protein kinase receptor R3, activin receptor-like kinase 1, ALK-1, TGF-B superfamily receptor type I, TSR-I, SKR3, ACVRLK1)

CAT#: ALK1
Enzyme: Human ALK1
Substrate: Casein, 20 mg/ml
ATP 10 μM
Reaction:

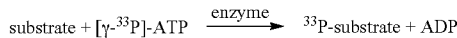

$$\text{substrate} + [\gamma\text{-}^{33}P]\text{-ATP} \xrightarrow{\text{enzyme}} {}^{33}P\text{-substrate} + ADP$$

HPLC/MS method:
Column: Chromolith SpeedROD RP-18e, 50×4.6 mm$^2$
Gradient: A:B=96:4 to 0:100
Flow rate: 2.4 ml/min
Eluent A: water+0.05% of formic acid
Eluent B: acetonitrile+0.04% of formic acid
Wavelength: 220 nm
Mass spectroscopy: positive mode
m.p.=melting point
MS (ESI): mass spectroscopy (electrospray ionisation)
MS (EI): mass spectroscopy (electron impact ionisation)

Above and below, all temperatures are indicated in ° C. In the following examples, "conventional work-up" means: water is added if necessary, the pH is adjusted, if necessary, depending on the constitution of the end product, to values between 2 and 10, the mixture is extracted with ethyl acetate or dichloromethane, the phases are separated, the organic phase is dried over sodium sulfate, evaporated and purified by chromatography on silica gel and/or by crystallisation.

Syntheses

The compound according to the invention is prepared by Pd-catalysed cross-coupling of starting material 1 (4-bromo-2,7-naphthyridin-1-ylamine) with starting material 2 (1-benzenesulfonyl-2-methyl-3-(4,4,5,5-tetramethyl-1,3,2-dioxaborolan-2-yl)-1H-pyrrolo[2,3-b]pyridine) and subsequent cleaving off of the benzenesulfonyl group using alcohols under basic conditions.

Starting Material 1:

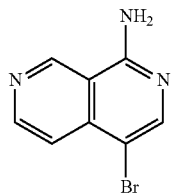 [SMILES: Nc1ncc(Br)c2ccncc12]

4-Bromo-2,7-naphthyridin-1-ylamine, CAS 959558-28-2, is commercially available and is prepared by bromination of 2,7-naphthyridin-1-ylamine using bromine in acetic acid.

Alternatively, the compound is prepared from 2H-2,7-naphthyridin-1-one CAS 67988-50-5, the hydrobromide CAS 950746-19-7 or the hydrochloride CAS 369648-60-2.

Bromination gives 4-bromo-2,7-naphthyridin-1(2H)-one CAS 959558-27-1, which is converted into 4-bromo-1-chloro-2,7-naphthyridine by chlorinating compounds, such as POCl$_3$ and/or PCl$_5$. Reaction with ammonia or ammonia equivalents gives 2,7-naphthyridin-1-ylamine.

Alternatively, 4-methylnicotinonitrile CAS 5444-01-9 is reacted with DMF acetal (for example CAS 4637-24-5 [dimethyl]), giving 4-((E)-2-dimethylamino-vinyl)nicotinonitrile CAS 36106-34-0, which is cyclised to 2,7-naphthyridin-1-ylamine.

Starting Material 2:

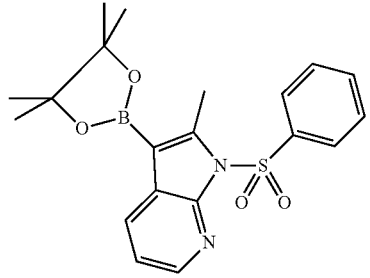 [SMILES: Cc1c(B2OC(C)(C)C(C)(C)O2)c2cccnc2n1S(=O)(=O)c1ccccc1]

1-(Benzenesulfonyl)-2-methyl-3-(4,4,5,5-tetramethyl-1,3,2-dioxaborolan-2-yl)-1H-pyrrolo[2,3-b]pyridine CAS 943324-08-1 is commercially available and is prepared from 3-iodo-2-methyl-1-(benzenesulfonyl)-7-azaindole CAS 943324-07-0 by Pd-catalysed reaction with bis(pinacolato)diboron CAS 73183-34-3 (Seefeld et al., WO 2007/076423 A2, page 170).

Alternatively, the compound 3-bromo-2-methyl-1-(benzenesulfonyl)-7-azaindole CAS 744209-37-8 is employed instead of 3-iodo-2-methyl-1-(benzenesulfonyl)-7-azaindole.

EXAMPLES

4-Bromo-2,7-naphthyridin-1-ylamine 940 ml of DMF dimethyl acetal are added to a solution of 200 g of 4-methylnicotinonitrile in 940 g of DMF, and the mixture is heated under reflux at 120-110 for 3 days. The mixture is cooled to 35° C., poured into 10 liters of ice-water and cooled at 4° C. for 16 h. The precipitate is filtered off, washed with water and dried, giving 263 g of 4-((E)-2-dimethylaminovinyl)nicotinonitrile; M~173.22 g/mol; M+H found 174, NMR corresponds.

810 g of ammonium formate are added to 253 g of 4-((E)-2-dimethylaminovinyl)nicotinonitrile in a 4 liter vessel. 300 ml of AcOH are then added, and the mixture is heated at 115° C. for 20 h. The mixture is cooled, 5 liters of water are added, and the mixture is extracted 10× with 0.5 liter of CH$_2$Cl$_2$. The aqueous phase is adjusted to ~pH 10 using 160 g of NaOH. The aqueous phase is extracted with MTB ether, the organic phase is separated off and dried over sodium sulfate. Removal of the solvent and drying gives 59 g of 2,7-naphthyridin-1-ylamine, M~145.16 g/mol, M+H found 146, NMR corresponds.

32 g of 2,7-naphthyridin-1-ylamine is dissolved in 200 ml of acetic acid at room temperature. 35 g of bromine in 200 ml of acetic acid are then added slowly that the temperature does not exceed 25°. The mixture is stirred for a further 60 minutes.

The suspension obtained is dissolved in 500 ml of water, and the pH is adjusted to pH 7-8 using 500 ml of 25% aqueous ammonia solution.

The mixture is stirred for 14 h. The brown precipitate is filtered off, washed with water and dried, giving 28.3 g of crude product. Purification by flash chromatography in ethyl acetate/methanol gives 18.5 g of 4-bromo-2,7-naphthyridin-1-ylamine, M~224.06 g/mol, M+H found 224.

1-(Benzenesulfonyl)-2-methyl-3-(4,4,5,5-tetramethyl-1,3,2-dioxaborolan-2-yl)-1H-pyrrolo[2,3-b]pyridine 4.8 ml of a 2M solution of lithium diisopropylamide in THF/heptane are added dropwise over the course of 60 min. to a solution of 1 g of 1-(benzenesulfonyl)-7-azaindole in 20 ml of THF at −70° C. under an N$_2$ atmosphere. The mixture is allowed to warm to 20° over the course of 50 minutes. The suspension is cooled to −70°, and a solution of 1.1, g of iodomethane in 20 ml of THF is added dropwise over the course of 20 minutes. The mixture is stirred at −70° for one hour and subsequently at room temperature for 14 h. The mixture is diluted with water and extracted with dichloromethane. The extract is dried over sodium sulfate, filtered, the solvent is removed and crystallised from cyclohexane, giving 0.68 g of 2-methyl-1-(benzenesulfonyl)-7-azaindole, M~272.32 g/mol, M+H found 273, NMR corresponds.

Bromination in DMF:

25 g of NBS in 75 ml of DMF are added to a solution of 34.8 g of 2-methyl-1-(benzenesulfonyl)-7-azaindole in 75 ml of DMF. The mixture is stirred at room temperature for 1 h, poured into water, the precipitate which has precipitated out is separated off, washed with water and dried, giving 42 g of 3-bromo-2-methyl-1-(benzenesulfonyl)-7-azaindole, M~351.22 g/mol, M+H found 351.

Bromination in Acetonitrile:

72 mg of NBS in 2 ml of CH$_3$CN are added to a solution of 100 mg of 2-methyl-1-(benzenesulfonyl)-7-azaindole in 3 ml of CH$_3$CN. The mixture is stirred at room temperature for 20 h, poured into water, the precipitate which has precipitated out is separated off and dried, giving 93 mg of 3-bromo-2-methyl-1-(benzenesulfonyl)-7-azaindole, M~351.22 g/mol, M+H found 351.

2.6 g of potassium acetate and 300 mg of PdCl$_2$(PPh$_3$)$_2$ are added to a solution of 3 g of 3-bromo-2-methyl-1-(benzenesulfonyl)-7-azaindole and 2.9 g of bispinacolatodiboron in 30 ml of diethylene glycol dimethyl ether. The mixture is heated at 120° for 3 h, diluted with water and extracted with ethyl acetate. The organic phase is dried over sodium sulfate, filtered off, and the solvent is removed, giving 3 g of 1-(benzenesulfonyl)-2-methyl-3-(4,4,5,5-tetramethyl-1,3,2-dioxaborolan-2-yl)-1H-pyrrolo[2,3-b]pyridine, M~398.29 g/mol, M+H found 399.

4-(1-Benzenesulfonyl-2-methyl-1H-pyrrolo[2,3-b]pyridin-3-yl)-2,7-naphthyridin-1-ylamine

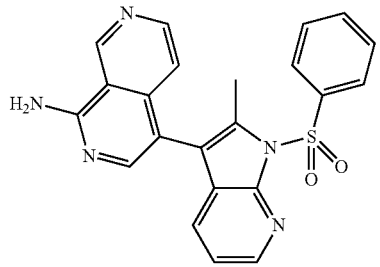 [SMILES: Cc1c(-c2cnc(N)c3cnccc23)c2cccnc2n1S(=O)(=O)c1ccccc1]

23.7 g of tripotassium phosphate and 3.2 g of trans-dichlorobis(tricyclohexyl-phosphine)palladium(II) are added to a solution of 12.5 g of 4-bromo-2,7-naphthyridin-1-ylamine in 400 ml of diglyme and 15 ml of water. The mixture is heated to 125°, and 25 g of 1-(benzenesulfonyl)-2-methyl-3-(4,4,5,5-tetramethyl-1,3,2-dioxaborolan-2-yl)-1H-pyrrolo[2,3-b]pyridine in 100 ml of diglyme are added dropwise over the course of 30 minutes. The mixture is stirred at 125° for 3 h, at room temperature for 20 h and the solvent is subsequently removed and the mixture is subjected to conventional work-up. The product is purified by means of flash chromatography over 330 g of silica with a methanol gradient in ethyl acetate with 200 ml/min with UV detection at 254 nm, giving a pure fraction (5.1 g) and a contaminated fraction (6.5 g) of 4-(1-benzenesulfonyl-2-methyl-1H-pyrrolo[2,3-b]pyridin-3-yl)-2,7-naphthyridin-1-ylamine, M~415.47 g/mol, M+H found 416.

4-(2-Methyl-1H-pyrrolo[2,3-b]pyridin-3-yl)-2,7-naphthyridin-1-ylamine

A mixture of 23 g of 4-(1-benzenesulfonyl-2-methyl-1H-pyrrolo[2,3-b]pyridin-3-yl)-2,7-naphthyridin-1-ylamine and 26 g of caesium carbonate in 400 ml of THF/trifluoroethanol (1:1 vol) is heated under reflux for 20 h. The mixture is cooled, the solvent is removed, and the product is purified by means of flash chromatography over 220 g of silica with a methanol gradient in ethyl acetate with 150 ml/min with UV detection at 254 nm, giving 12.2 g of 4-(2-methyl-1H-pyrrolo[2,3-b]pyridin-3-yl)-2,7-naphthyridin-1-ylamine, M~275.31, M+H found 276.2;

$^1$H NMR (500 MHz, DMSO-d$_6$) ppm [ppm] 11.75 (s, 1H), 9.64-9.57 (m, 1H), 8.50 (d, J=5.8, 1H), 8.15 (dd, J=4.7, 1.5, 1H), 7.98 (s, 1H), 7.42 (dd, J=7.8, 1.6, 1H), 7.31 (s, 2H), 7.18 (dd, J=5.8, 0.9, 1H), 6.97 (dd, J=7.8, 4.7, 1H), 2.29 (s, 3H).

TABLE 2

Inhibition of TGF-beta kinase ALK5 and ALK1
Comparison of the compound according to the invention with compounds from the prior art

| Compound No. | Structure | IC$_{50}$ [nM] [TGF-beta] enzym. ALK5 | IC$_{50}$ [nM] [TGF-beta] cell. | IC$_{50}$ [nM] [ALK1] |
|---|---|---|---|---|
| "A32" from WO 2012/104007 | NH$_2$ structure | 43 | 770 | n.d |

TABLE 2-continued

Inhibition of TGF-beta kinase ALK5 and ALK1
Comparison of the compound according to the invention with compounds from the prior art

| Compound No. | Structure | IC$_{50}$ [nM] [TGF-beta] enzym. ALK5 | IC$_{50}$ [nM] [TGF-beta] cell. | IC$_{50}$ [nM] [ALK1] |
|---|---|---|---|---|
| "A24" from WO 2012/104007 | 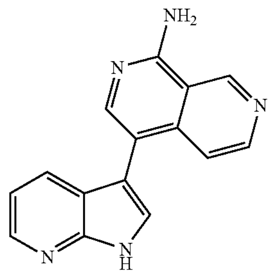 [SMILES: Nc1ncc(-c2c[nH]c3ncccc23)c2ccncc12] | 13 | 72 | n.d. |
| "A13" from WO 2012/104007 | 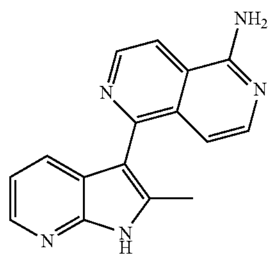 [SMILES: Cc1[nH]c2ncccc2c1-c1nccc2c(N)nccc12] | 16 | 160 | 200 |
| 4-(2-Methyl-1H-pyrrolo[2,3-b]-pyridin-3-yl)-2,7-naphthyridin-1-yl-amine | 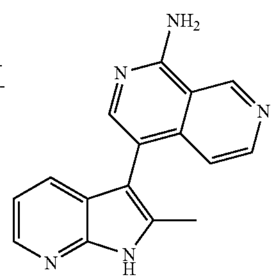 | 4.6 | 28 | 79 |

The following examples relate to medicaments:

Example A

Injection Vials

A solution of 100 g of the compound according to the invention and 5 g of disodium hydrogenphosphate in 3 l of bidistilled water is adjusted to pH 6.5 using 2 N hydrochloric acid, sterile filtered, transferred into injection vials, lyophilised under sterile conditions and sealed under sterile conditions. Each injection vial contains 5 mg of active compound.

Example B

Suppositories

A mixture of 20 g of the compound according to the invention with 100 g of soya lecithin and 1400 g of cocoa butter is melted, poured into moulds and allowed to cool. Each suppository contains 20 mg of active compound.

Example C

Solution

A solution is prepared from 1 g of the compound according to the invention, 9.38 g of NaH$_2$PO$_4$.2H$_2$O, 28.48 g of Na$_2$HPO$_4$.12 H$_2$O and 0.1 g of benzalkonium chloride in 940 ml of bidistilled water. The pH is adjusted to 6.8, and the solution is made up to 1 l and sterilised by irradiation. This solution can be used in the form of eye drops.

Example D

Ointment 500 mg of the compound according to the invention are mixed with 99.5 g of Vaseline under aseptic conditions.

Example E

Tablets

A mixture of 1 kg of the compound according to the invention, 4 kg of lactose, 1.2 kg of potato starch, 0.2 kg of talc and 0.1 kg of magnesium stearate is pressed in a conventional manner to give tablets in such a way that each tablet contains 10 mg of active compound.

Example F

Dragees

Tablets are pressed analogously to Example E and subsequently coated in a conventional manner with a coating of sucrose, potato starch, talc, tragacanth and dye.

Example G

Capsules 2 kg of the compound according to the invention are introduced into hard gelatine capsules in a conventional manner in such a way that each capsule contains 20 mg of the active compound.

Example H

Ampoules

A solution of 1 kg of the compound according to the invention in 60 l of bidistilled water is sterile filtered, transferred into ampoules, lyophilised under sterile conditions and sealed under sterile conditions. Each ampoule contains 10 mg of active compound.

The invention claimed is:

1. The compound 4-(2-methyl-1H-pyrrolo[2,3-b]pyridin-3-yl)-2,7-naphthyridin-1-ylamine

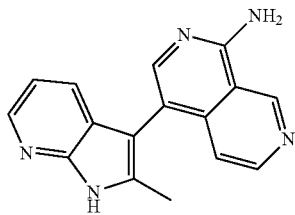 [SMILES: Cc1[nH]c2ncccc2c1-c1cnc(N)c2cnccc12]

or a pharmaceutically acceptable salt or tautomer thereof.

2. A pharmaceutical composition comprising 4-(2-methyl-1H-pyrrolo[2,3-b]pyridin-3-yl)-2,7-naphthyridin-1-ylamine or a pharmaceutically acceptable salt or tautomer thereof according to claim 1, and one or more pharmaceutically acceptable excipients and/or adjuvants.

3. A method for treating a tumour, tumour growth, tumour metastases or AIDS, comprising administering to a subject in need thereof an effective amount of the compound 4-(2-methyl-1H-pyrrolo[2,3-b]pyridin-3-yl)-2,7-naphthyridin-1-ylamine or a pharmaceutically acceptable salt or tautomer thereof according to claim 1.

4. A method for treating a tumour, comprising administering to a subject in need thereof an effective amount of the compound 4-(2-methyl-1H-pyrrolo[2,3-b]pyridin-3-yl)-2,7-naphthyridin-1-ylamine or a pharmaceutically acceptable salt or tautomer thereof according to claim 1 in combination with a compound selected from the group consisting of 1) oestrogen receptor modulator, 2) androgen receptor modulator, 3) retinoid receptor modulator, 4) cytotoxic agent, 5) antiproliferative agent, 6) prenyl-protein-transferase inhibitor, 7) HMG-CoA reductase inhibitor, 8) HIV protease inhibitor, 9) reverse transcriptase inhibitor and 10) further angiogenesis inhibitors.

5. A method for treating a tumour, comprising administering to a subject in need thereof an effective amount of the compound 4-(2-methyl-1H-pyrrolo[2,3-b]pyridin-3-yl)-2,7-naphthyridin-1-ylamine or a pharmaceutically acceptable salt or tautomer thereof according to claim 1 in combination with radiotherapy and a compound selected from the group consisting of 1) oestrogen receptor modulator, 2) androgen receptor modulator, 3) retinoid receptor modulator, 4) cytotoxic agent, 5) antiproliferative agent, 6) prenyl-protein transferase inhibitor, 7) HMG-CoA reductase inhibitor, 8) HIV protease inhibitor, 9) reverse transcriptase inhibitor and 10) further angiogenesis inhibitors.

6. A method for treating a tumour, comprising administering to a subject in need thereof an effective amount of the compound 4-(2-methyl-1H-pyrrolo[2,3-b]pyridin-3-yl)-2,7-naphthyridin-1-ylamine or a pharmaceutically acceptable salt or tautomer thereof according to claim 1 in combination with an immune modulator compound.

7. A method for treating a tumour, comprising administering to a subject in need thereof an effective amount of the compound 4-(2-methyl-1H-pyrrolo[2,3-b]pyridin-3-yl)-2,7-naphthyridin-1-ylamine or a pharmaceutically acceptable salt or tautomer thereof according to claim 1 in combination with radiotherapy and an immune modulator compound.

8. A method for treating a tumour, tumour growth, tumour metastases or AIDS, wherein prevention is excluded, comprising administering to a subject in need thereof an effective amount of the compound 4-(2-methyl-1H-pyrrolo[2,3-b]pyridin-3-yl)-2,7-naphthyridin-1-ylamine or a pharmaceutically acceptable salt or tautomer according to claim 1.

* * * * *